United States Patent [19]

Ichinohe et al.

[11] Patent Number: 6,015,870
[45] Date of Patent: Jan. 18, 2000

[54] PROCESS FOR PREPARING POLYSULFIDE SILANES

[75] Inventors: Shoji Ichinohe; Hideyoshi Yanagisawa; Akira Yamamoto, all of Usui-gun, Japan

[73] Assignee: Shin-Etsu Chemical Co., Ltd., Tokyo, Japan

[21] Appl. No.: 09/161,290

[22] Filed: Sep. 28, 1998

[30] Foreign Application Priority Data

Sep. 26, 1997 [JP] Japan .................................. 9-279656

[51] Int. Cl.[7] .................................................. C08G 77/22

[52] U.S. Cl. .............................. 528/30; 528/34; 528/373; 528/388; 556/427

[58] Field of Search ............................... 556/427; 528/30, 528/34, 373, 388

[56] References Cited

U.S. PATENT DOCUMENTS

| | | | |
|---|---|---|---|
| 4,374,943 | 2/1983 | Williams | 523/211 |
| 5,663,395 | 9/1997 | Goebel et al. | |
| 5,859,275 | 1/1999 | Munzenberg et al. | 556/427 |

*Primary Examiner*—Melvyn I. Marquis
*Attorney, Agent, or Firm*—Millen, White, Zelano & Branigan, P.C.

[57] ABSTRACT

Polysulfide silanes: $(RO)_3SiC_3H_6S_xC_3H_6Si(OR)_3$ are reacted with an anhydrous sulfur compound: $M^1_2S$ or $M^2S$ and a halogenoalkoxysilane: $XC_3H_6Si(OR)_3$ to form polysulfide silanes: $(RO)_3SiC_3H_6S_yC_3H_6Si(OR)_3$ wherein R is methyl or ethyl, x is a positive number of 3 to 6 on the average, $M^1$ is an alkali metal or ammonium, $M^2$ is an alkaline earth metal or zinc, X is a halogen, and y is a positive number less than x on the average. Short chain polysulfide silanes can be prepared with the industrial advantages of safety, high yields and low cost.

20 Claims, No Drawings

PROCESS FOR PREPARING POLYSULFIDE SILANES

This invention relates to a process for preparing polysulfide silanes, especially short chain polysulfide silanes.

BACKGROUND OF THE INVENTION

Bis(triethoxysilylpropyl) tetrasulfide is commonly used in silica-blended tires as an agent for coupling rubber with silica. This compound, however, has the problem that when it is kneaded with rubber and silica at elevated temperature, it causes the blend to increase its Mooney viscosity so that the blend becomes difficult to work.

To overcome this problem, short chain polysulfide silanes such as bis(triethoxysilylpropyl) disulfide were proposed. JP-A 169774/1997 discloses a process for preparing a disulfide silane using sodium cyanide (NaCN). This process, however, uses a toxic reagent. There is a desire to have an alternative, inexpensive and safe process for preparing short chain polysulfide silanes.

SUMMARY OF THE INVENTION

The present invention pertains to the preparation of short chain polysulfide silanes from polysulfide silanes of the following general formula (1):

$$(RO)_3SiC_3H_6S_xC_3H_6Si(OR)_3 \quad (1)$$

wherein R is methyl or ethyl, and letter x is a positive number of 3 to 6 on the average, while changing the distribution of sulfide chains thereof, and especially a process for preparing from polysulfide silanes of formula (1) short chain polysulfide silanes having a shorter sulfide chain than the starting polysulfide silanes.

Therefore, an object of the present invention is to provide a novel and improved process for preparing from polysulfide silanes of formula (1) short chain polysulfide silanes having a shorter average sulfide chain than the starting polysulfide silanes, especially short chain polysulfide silanes having 2 or 3 sulfide chains on the average.

According to the invention, there is provided a process for preparing polysulfide silanes by reacting polysulfide silanes of the following general formula (1):

$$(RO)_3SiC_3H_6S_xC_3H_6Si(OR)_3 \quad (1)$$

wherein R is methyl or ethyl, and letter x is a positive number of 3 to 6 on the average, especially equal to 4 on the average, with at least one anhydrous sulfur compound selected from sulfur compounds of the formulae: $M^1_2S$ and $M^2S$ wherein $M^1$ is an alkali metal or ammonium and $M^2$ is an alkaline earth metal or zinc, and a halogenoalkoxysilane of the following general formula (2):

$$XC_3H_6Si(OR)_3 \quad (2)$$

wherein X is a halogen atom and R is methyl or ethyl, to form polysulfide silanes of the following general formula (3):

$$(RO)_3SiC_3H_6S_yC_3H_6Si(OR)_3 \quad (3)$$

wherein R is as defined above and y is a positive number less than x (that is, x>y) on the average.

Preferably, the polysulfide silanes of formula (1) are first reacted with the anhydrous sulfur compound, optionally at an elevated temperature, until a polysulfide distribution reaches equilibrium, and the halogenoalkoxysilane of formula (2) is then reacted therewith, thereby forming short chain polysulfide silanes of formula (3) wherein y is a positive number of 2 to 3 on the average. The short chain polysulfide silanes can be produced in a safe manner, in high yields and at low cost.

DETAILED DESCRIPTION OF THE INVENTION

According to the process of the invention, polysulfide silanes of formula (3) are obtained by reacting polysulfide silanes of formula (1), an anhydrous sulfur compound of the formulae: $M^1_2S$ or $M^2S$ and a halogenoalkoxysilane of formula (2).

The polysulfide silanes used as the starting reactant are represented by the general formula (1):

$$(RO)_3SiC_3H_6S_xC_3H_6Si(OR)_3 \quad (1)$$

wherein R is methyl or ethyl, and letter x is a positive number of 3 to 6 on the average. Polysulfide silanes of formula (1) wherein x is 4 on the average are especially suitable because they are inexpensive.

The anhydrous sulfur compound is selected from sulfides of the formulae: $M^1_2S$ and $M^2S$ wherein $M^1$ is an alkali metal or ammonium and $M^2$ is an alkaline earth metal or zinc. Exemplary sulfides are $Na_2S$, $K_2S$, $Li_2S$, $(NH_4)_2S$, CaS, MgS and ZnS, with the $Na_2S$ being especially preferred.

In one preferred embodiment of the invention, the polysulfide silanes of formula (1) are first reacted with the sulfide. For this reaction, a solvent may or may not be used. When used, those solvents which allow the sulfide to be partially dissolved in the reaction system are advantageous. Useful solvents include aliphatic hydrocarbon solvents such as pentane and hexane, aromatic hydrocarbon solvents such as benzene, toluene and xylene, ethers such as diethyl ether and dibenzyl ether, esters and ketones. Advantageous solvents are alcohols such as methanol, ethanol, propanol, butanol, benzyl alcohol and phenol, with the methanol and ethanol being most advantageous. The reaction temperature may range from room temperature to 150° C., preferably from 60° C. to 100° C. Reaction is advantageously carried out under solvent reflux, especially under ethanol reflux. The reaction time is 30 minutes or longer although a reaction time within 2 hours is sufficient under ethanol reflux conditions.

The reaction of the polysulfide silanes of formula (1) with the sulfide is an equilibration reaction. For example, when a tetrasulfide silane is reacted with $Na_2S$ under ethanol reflux, the reaction proceeds according to the following scheme.

$$A \times Na_2S + B \times (C_2H_5O)_3SiCH_6S_4C_3H_6Si(OC_2H_5)_3 \rightarrow A \times Na_2S_c + B \times (C_2H_5O)_3SiC_3H_6S_cC_3H_6Si(OC_2H_5)_3$$

Herein, c is $c=(A+4B)/(A+B)$.

For instance, when 1 mol of tetrasulfide silane is reacted with 1 mol of $Na_2S$, c is equal to 2.5.

It is evident from the above reaction scheme that when a tetrasulfide silane is used in the inventive process, a polysulfide silane product having any desired number of polysulfide chains in the range from an average disulfide silane to an average tetrasulfide silane can be obtained by controlling the reaction molar ratio of the tetrasulfide silane to $Na_2S$.

In the preferred embodiment of the present invention, after the completion of the above equilibration reaction, that is, after equilibrium is reached, the reaction product is reacted with a halogenoalkoxysilane of the following general formula (2):

$$XC_3H_6Si(OR)_3 \quad (2)$$

wherein X is a halogen atom and R is methyl or ethyl.

The amount of the halogenoalkoxysilane added may be determined as appropriate. For example, after the completion of equilibration reaction according to the above reaction scheme, 2A mol of the halogenoalkoxysilane is reacted, thereby forming (A+B) mol of a polysulfide silane. The reaction temperature may range from room temperature to 150° C., preferably from 60° C. to 100° C. Reaction is advantageously carried out in the above-described solvent, especially under ethanol reflux. The reaction time is 30 minutes to 20 hours, preferably 2 to 7 hours.

Thereafter, the solvent is distilled off in vacuum, and the salt formed is filtered off. Then the end product, that is, a polysulfide silane of the general formula (3):

$$(RO)_3SiC_3H_6S_yC_3H_6Si(OR)_3 \quad (3)$$

is obtained in high yields. Herein R is as defined above and y is a positive number satisfying x>y on the average, especially a positive number of 2 to 3 on the average. Accordingly, the process of the invention is useful in the preparation of short chain polysulfide silanes of formula (3) wherein y is a positive number of 2 to 3 on the average.

According to the present invention, from polysulfide silanes of formula (1), short chain polysulfide silanes having a shorter average polysulfide chain than the starting polysulfide silanes can be prepared with industrial advantages including safety, high yields and low cost.

EXAMPLE

Examples of the invention are given below by way of illustration and not by way of limitation.

Example 1

A 3-liter flask was charged with 538 g (1 mol) of an average tetrasulfide silane represented by the average compositional formula:

$$(CH_3CH_2O)_3SiC_3H_6S_4C_3H_6Si(OCH_2CH_3)_3,$$

78 g (1 mol) of anhydrous sodium sulfide, and 400 g of ethanol. Reaction was effected for 1 hour under ethanol reflux. Subsequently, 481 g (2 mol) of chloropropyltriethoxysilane was added dropwise under ethanol reflux. The reaction solution was ripened for 5 hours under ethanol reflux. The ethanol was distilled off in vacuum, and the sodium chloride formed was filtered off. There was obtained 940 g (yield 96%) of a polysulfide silane product having an average sulfide chain number of 2.5 represented by the following average compositional formula.

$$(CH_3CH_2)_3SiC_3H_6S_{2.5}C_3H_6Si(OCH_2CH_3)_3$$

The starting reactant and the polysulfide silane product were analyzed by super-critical chromatography, finding that they were mixtures of polysulfide silanes as reported below.

| Starting reactant | |
|---|---|
| Disulfide silane | 18% |
| Trisulfide silane | 30% |
| Tetrasulfide silane | 25% |
| Pentasulfide silane | 17% |
| Hexasulfide silane | 6% |
| Heptasulfide silane | 3% |
| Octasulfide silane | 1% |
| Product | |
| Disulfide silane | 51% |
| Trisulfide silane | 31% |
| Tetrasulfide silane | 13% |
| Penta and higher sulfide silanes ($\geq S_5$) | 5% |

Example 2

The procedure of Example 1 was repeated except that the average tetrasulfide silane and anhydrous sodium sulfide were replaced by 570 g (1 mol) of an average pentasulfide silane and 110 g (1 mol) of anhydrous potassium sulfide, respectively. There was obtained 950 g (yield 94%) of a trisulfide silane product having an average sulfide chain number of 3.

The starting reactant and the sulfide silane product were found to be mixtures as reported below.

| Starting reactant | |
|---|---|
| Disulfide silane | 4% |
| Trisulfide silane | 18% |
| Tetrasulfide silane | 33% |
| Pentasulfide silane | 29% |
| Hexasulfide silane | 14% |
| Heptasulfide silane | 5% |
| Octasulfide silane | 1% |
| Product | |
| Disulfide silane | 33% |
| Trisulfide silane | 32% |
| Tetrasulfide silane | 19% |
| Penta and higher sulfide silanes ($\geq S_5$) | 16% |

Example 3

The procedure of Example 1 was repeated except that the anhydrous sodium sulfide was replaced by anhydrous potassium sulfide. There was obtained 930 g (yield 95%) of a polysulfide silane product having an average sulfide chain number of 2.5. The polysulfide silane product was found to be a mixture as reported below.

| Product | |
|---|---|
| Disulfide silane | 53% |
| Trisulfide silane | 31% |
| Tetrasulfide silane | 12% |
| Penta and higher sulfide silanes ($\geq S_5$) | 4% |

Example 4

The procedure of Example 1 was repeated except that the average tetrasulfide silane of ethoxy type was replaced by 510 g (1 mol) of an average tetrasulfide silane of methoxy type. There was obtained 920 g (yield 94%) of a polysulfide silane product having an average sulfide chain number of 2.5. The polysulfide silane product was found to be a mixture as reported below.

| Product | |
|---|---|
| Disulfide silane | 55% |
| Trisulfide silane | 30% |
| Tetrasulfide silane | 11% |
| Penta and higher sulfide silanes ($\geq S_5$) | 4% |

Example 5

The procedure of Example 1 was repeated except that the anhydrous sodium sulfide was replaced by 72 g (1 mol) of anhydrous potassium sulfide. There was obtained 930 g (yield 95%) of a polysulfide silane product having an average sulfide chain number of 2.5. The polysulfide silane product was found to be a mixture as reported below.

| Product | |
|---|---|
| Disulfide silane | 56% |
| Trisulfide silane | 29% |
| Tetrasulfide silane | 11% |
| Penta and higher sulfide silanes ($\geq S_5$) | 4% |

Japanese Patent Application No. 279656/1997 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. A process for preparing polysulfide silanes, comprising reacting polysulfide silanes of formula (1)

$$(RO)_3SiC_3H_6S_xC_3H_6Si(OR)_3 \quad (1)$$

wherein R is methyl or ethyl, and x is a positive number of 3 to 6 on the average, with at least one anhydrous sulfur compound selected from sulfur compounds of formulae $M^1_2S$ and $M^2S$ wherein $M^1$ is an alkali metal or ammonium and $M^2$ is an alkaline earth metal or zinc, and a halogenoalkoxysilane of general formula (2)

$$XC_3H_6Si(OR)_3 \quad (2)$$

wherein X is halogen and R is methyl or ethyl, to form polysulfide silanes of formula (3)

$$(RO)_3SiC_3H_6S_yC_3H_6Si(OR)_3 \quad (3)$$

wherein R is as defined above and y is a positive number less than x on the average.

2. The process of claim 1 wherein the polysulfide silanes of formula (1) are first reacted with at least one anhydrous sulfur compound selected from $M^1_2S$ and $M^2S$ until a polysulfide distribution reaches equilibrium, and the halogenoalkoxysilane of formula (2) is then reacted therewith, thereby forming short chain polysulfide silanes of formula (3) wherein y is a positive number of 2 to 3 on the average.

3. The process of claim 2 wherein the polysulfide silanes of formula (1) wherein x is 4 on the average are first reacted with at least one anhydrous sulfur compound selected from $M^1_2S$ and $M^2S$ until a polysulfide distribution reaches equilibrium, and a chloropropylsilane is then reacted therewith, thereby forming short chain polysulfide silanes of formula (3) wherein y is a positive number of 2 to 3 on the average.

4. The process of claim 1, wherein the sulfur compound of $M^1_2S$ or $M^2S$ is $Na_2S$, $K_2S$, $Li_2S$, $(NH_4)_2S$, CaS, MgS or ZnS.

5. The process of claim 4, wherein the sulfur compound of $M^1_2S$ is $Na_2S$.

6. The process of claim 2, wherein the polysulfide silanes of formula 1 are reacted with the sulfur compound in a solvent which is an aliphatic hydrocarbon, an aromatic hydrocarbon, an ether, an ester, a ketone, or an alcohol.

7. The process of claim 6, wherein the aliphatice hydrocarbon is pentane or hexane, the aromatic hydrocarbon is benzene, toluene or xylene, or the ether is diethyl ether or dibenzyl ether.

8. The process of claim 6, wherein the alcohol is methanol, ethanol, propanol, butanol, benzyl alcohol or phenol.

9. the process of claim 8, wherein the alcohol is methanol or ethanol.

10. The process of claim 2, wherein the polysulfide silanes of formula 1 are reacted with the sulfur compound at 60° C. to 100° C.

11. The process of claim 2, wherein the polysulfide silanes of formula 1 are reacted with the sulfur compound under ethanol reflux.

12. The process of claim 2, wherein the product of the first reaction is reacted with the halogenoalkoxysilane of formula (2) at 60° C. to the 100° C.

13. The process of claim 2, wherein the product of the first reaction is reacted with the halogenoalkoxysilane of formula (2) in solvent whcih is an aliphatic hydrocarbon, an aromatic hydrocarbon, an ether, an ester, a ketone, or an alcohol.

14. The process of claim 13, wherein the aliphatic hydrocarbon is pentane or hexane, the aromatic hydrocarbon is benzene, toluene or xylene, or the ether is diethyl ether or dibenzyl ether.

15. The process of calim 13, wherein the alcohol is methane, ethanol, propanol, butanol, benzyl, alcohol pr phenol.

16. The process of claim 15, wherein the alcohol is methanol or ethanol.

17. The process of claim 2, wherein the product of the first reaction is reacted with the halogenoalkoxysilane of formula (2) under ethanol reflux.

18. The process of claim 2, wherein the product of the first reaction is reacted with the halogenoalkoxysilane of formula (2) for 2 to 7 hours.

19. The process of claim 1, wherein the halogenalkoxysilane is chloropropyltriethoxysilane.

20. The process of claim 2, wherein the ploysulfide silanes of formula (1) are reacted with the sulfur compound for 30 minutes to 2 hours.

* * * * *